United States Patent [19]

Al-Shaar et al.

[11] Patent Number: 4,659,727

[45] Date of Patent: Apr. 21, 1987

[54] ETHENE DERIVATIVES

[75] Inventors: Adnan H. Al-Shaar, Benfleet; Barbara J. Broughton, Croydon; Robert K. Chambers, Erith; David W. Gilmour, Greenford; Diane M. Kelsey; Peter Lowden, both of Chelmsford; Edward Lunt, Clapton; David J. Lythgoe, Gidea Park; Ian McClenaghan, Ingrave; Duncan C. McDougall, Ilford; Libert C. Saunders, Grays; Keith A. J. Stuttle, Rochford; Peter J. Warne, South Woodford, all of England

[73] Assignee: May & Baker Limited, Essex, England

[21] Appl. No.: 774,467

[22] Filed: Sep. 10, 1985

[30] Foreign Application Priority Data

Sep. 11, 1984 [GB] United Kingdom ............... 8422916

[51] Int. Cl.$^4$ ................. C07D 277/42; A61K 31/425
[52] U.S. Cl. ..................................... 514/370; 548/197
[58] Field of Search ............... 548/197; 514/370

[56] References Cited

U.S. PATENT DOCUMENTS 1,173,097  7/1964  Herrling et al. .................... 548/197

FOREIGN PATENT DOCUMENTS 2020654  11/1979  United Kingdom .
2063862  6/1981  United Kingdom .

OTHER PUBLICATIONS

Derwent Patent Abstracts: 84002905/01 (JA 58198474A); 84002857/01 (JA 58198405A), May 1982. Tamura et al., Chemical & Pharmaceutical Bulletin: 26(10, 3167–3177 (1978); Okamato 22(2), 243–247 (1974).
Richardson et al., Journal Medicinal Chemistry: 15(12), 1203–1206 (1972).
Steck, Journal of Organic Chemistry: 27, 306–308 (1962).
Leysen et al., Journal of Heterocyclic Chemistry: 21, 1361–1366 (1984); Leysen et al., 21, 401–406 (1984); Saint-Ruf et al., 16, 1021–1024 (1979).
Rajappa et al., Indian Journal of Chemistry: 8, 499–501 (1970).

Primary Examiner—John M. Ford
Attorney, Agent, or Firm—Stevens, Davis, Miller & Mosher

[57] ABSTRACT

Ethene derivatives of the formula:

$$[R^5(R^1CR^4=CR^2R^3)_m]_n \qquad \text{I}$$

wherein $R^5$ represents optionally substituted heterocyclyl or a group $-CR^4=CR^2R^3$, or optionally substituted aryl, heterocyclylalkyl or arylalkyl and $R^1$ represents $-NR^6-$ wherein $R^6$ represents hydrogen or optionally substituted alkyl or aryl, or $R^5$ represents a quinonoidal group, and $R^1$ represents $=N-$, $R^4$ represents hydrogen, alkoxy, alkylthio, trifluoromethyl or optionally substituted alkyl or aryl, $R^2$ represents cyano, formyl, alkoxycarbonyl, alkylsulphonyl, dialkylcarbamoyl, dialkylthiocarbamoyl, aryloxycarbonyl, arylsulphinyl or arylsulphonyl, $R^3$ represents a group $R^2$ or hydrogen, nitro or optionally substituted aryl or aroyl or alkanoyl, and m and n are 1 or 2, and pharmaceutically acceptable salts thereof, with the exclusion of certain compounds in which $R^5$ represents pyridyl, 5-halogenopyrid-2-yl or 1,2,4-triazolo[4,3-a]-quinoline possess useful pharmacological properties.

3 Claims, No Drawings

ETHENE DERIVATIVES

This invention relates to new therapeutically useful ethene derivatives, to a process for their preparation, to pharmaceutical compositions containing them, and to their use as pharmaceuticals.

The new ethene derivatives are compounds of the general formula:

$$[R^5(R^1CR^4\!\!=\!\!CR^2R^3)_m]_n \qquad \text{I}$$

wherein $R^5$ represents a heterocyclyl group, containing 1, 2 or 3 rings and 1 or more heteroatoms selected from nitrogen, oxygen, sulphur and selenium atoms, which is unsubstituted or substituted by one or more substituents $R^8$ [which may be the same or different and each represents a halogen (i.e. fluorine, chlorine, bromine or iodine) atom or an amino, carboxy, cyano, nitro, hydroxy, oxo, formyl, trifluoromethyl, aryl, aryloxy, arylthio, benzyloxycarbonylamino, sulphamoyl, tetrazol-5-yl, carbamoyl, thiocarbamoyl, arylcarbamoyl or aroyl group, or a straight- or branched-chain alkyl group containing from 1 to 10 carbon atoms, or a straight- or branched-chain alkoxy, alkylthio, alkylsulphinyl, alkylsulphonyl, alkylamino, alkylsulphamoyl, arylalkyl or arylalkoxy group containing from 1 to 10 carbon atoms in the alkyl moiety, a straight- or branched-chain alkanoyl, alkoxycarbonyl, alkoxycarbonylamino, alkylcarbamoyl or alkanoylamino group containing from 2 to 6 carbon atoms, an N-benzyloxycarbonyl-N-alkylamino group wherein the alkylamino moiety is straight or branched and contains from 1 to 6 carbon atoms, or a dialkylsulphamoyl, dialkylamino or dialkylcarbamoyl group wherein the alkyl moieties may be straight or branched and may each contain from 1 to 6 carbon atoms and may be linked together to form a ring, preferably a 5- to 9-membered ring, or a group of the formula $-CR^4\!\!=\!\!CR^2R^3$], or an aryl group which is unsubstituted or substituted by one or more substituents $R^8$ (as hereinbefore defined), or a heterocyclylalkyl or arylalkyl group wherein the heterocyclyl or aryl moiety is as hereinbefore defined and the alkyl moiety is straight or branched and contains 1 or 2 carbon atoms, and $R^1$ represents a group of the general formula:

$$-NR^6- \qquad \text{II}$$

wherein $R^6$ represents a hydrogen atom or a straight- or branched-chain alkyl group containing from 1 to 6 carbon atoms wwhich may be substituted by one or more substituents $R^8$ (as hereinbefore defined) or an aryl group which may be substituted by one or more substituents $R^8$ (as hereinbefore defined), or $R^5$ represents a quinonoidal group $R^7$ derived from a nitrogen-containing heterocyclyl group within the definition of $R^5$ as hereinbefore defined, bearing on said ring-nitrogen atom a substituent selected from straight- and branched-chain alkyl groups containing from 1 to 6 carbon atoms which may be substituted by one or more substituents $R^8$ (as hereinbefore defined), and aryl groups which may be substituted by one or more substituents $R^8$ (as hereinbefore defined), and $R^1$ represents a nitrogen atom of the form $=\!\!N\!\!-$, $R^4$ represents a hydrogen atom or a straight- or branched-chain alkoxy or alkylthio group containing from 1 to 6 carbon atoms, a trifluoromethyl group or a straight- or branched-chain alkyl group containing from 1 to 6 carbon atoms which may be substituted by one or more substituents $R^8$ (as hereinbefore defined), or an aryl group which may be substituted by one or more substituents $R^8$ (as hereinbefore defined), $R^2$ represents a cyano or formyl group, a straight- or branched-chain alkoxycarbonyl or alkylsulphonyl group containing up to 6 carbon atoms, or a dialkylcarbamoyl or dialkylthiocarbamoyl group wherein the alkyl groups may be the same or different and each may be straight or branched and each contains from 1 to 6 carbons atoms, or an aryloxycarbonyl, arylsulphinyl or arylsulphonyl group wherein the aryl moiety may be substituted by one or more substituents $R^8$ (as hereinbefore defined), $R^3$ represents a group within the definitiion of $R^2$ or a hydrogen atom or a nitro group or an aryl or aroyl group which may be substituted by one or more substituents $R^8$ (as hereinbefore defined) or a straight- or branched-chain alkanoyl group containing up to 6 carbon atoms, and m and n each represents 1 or 2, and pharmaceutically acceptable salts thereof, with the proviso that the following classes of compounds are excluded:

(i) compounds of formula I wherein $R^5$ represents a pyridyl group, which is unsubstituted or substituted by one or more substituents $R^9$ [which may be the same or different and each represents a halogen atom or an amino, carboxy, cyano, nitro, hydroxy, formyl, trifluoromethyl, aryl, aryloxy, arylthio, benzyloxycarbonylamino, sulphamoyl, tetrazol-5-yl, carbamoyl, thiocarbamoyl, arylcarbamoyl or aroyl group, or a straight- or branched-chain alkyl group containing from 1 to 6 carbon atoms, or a straight- or branched-chain alkoxy, alkylthio, alkylsulphonyl, alkylamino, alkylsulphamoyl or arylalkyl group containing from 1 to 6 carbon atoms in the alkyl moiety, a straight- or branched-chain alkanoyl, alkoxycarbonyl, alkoxycarbonylamino, alkylcarbamoyl or alkanoylamino group containing from 2 to 6 carbon atoms, an N-benzyloxycarbonyl-N-alkylamino group wherein the alkylamino moiety is straight or branched and contains from 1 to 6 carbon atoms, or a dialkylsulphamoyl, dialkylamino or dialkylcarbamoyl group wherein the alkyl moieties may be straight or branched and may each contain from 1 to 6 carbon atoms and may be linked together to form a ring], $R^2$ and $R^3$ may be the same or different and each represents a phenylsulphonyl group which may be unsubstituted or substituted by one or more substituents $R^9$ (as hereinbefore defined), $R^1$ represents a group of formula II, $R^4$ and $R^6$ represent hydrogen atoms and m and n both represent 1;

(ii) compounds of formula I wherein $R^5$ represents a 5-halogenopyrid-2-yl group, $R^2$ and $R^3$ both represent cyano groups, $R^1$ represents a group of formula II, $R^4$ and $R^6$ represent hydrogen atoms and m and n both represent 1; and (iii) compounds of formula I wherein $R^5$ represents a 1,2,4-triazolo[4,3-a]quinoline group which is unsubstituted or substituted by one or more substituents $R^{10}$ [which may be the same or different and each represents a halogen atom or an amino, carboxy, cyano, nitro, hydroxy, formyl, trifluoromethyl, aryl, aryloxy, arylthio, benzyloxycarbonylamino, sulphamoyl, tetrazol-5-yl, carbamoyl, thiocarbamoyl, arylcarbamoyl or aroyl group, or a straight- or branched-chain alkyl group containing from 1 to 6 carbon atoms, or a straight- or branched-chain alkoxy, alkylthio, alkylsulphinyl, alkylsulphonyl, alkylamino, alkylsulphamoyl or arylalkyl group containing from 1 to 6 carbon atoms in the alkyl moiety, a straight- or branched-chain alkanoyl, alkoxycarbonyl, alkoxycarbonylamino, alkylcarbamoyl or alkanoylamino group containing from 2 to 6 carbon atoms, an N-benzyloxycarbonyl-N-alkylamino group wherein the alkylamino moiety is straight or branched and contains from 1 to 6 carbon atoms, or a dialkylsulphamoyl, dialkylamino or dialkylcarbamoyl group wherein the alkyl moieties may be straight or branched and may each contain from 1 to 6 carbon atoms and may be linked together to form a ring], $R^2$ and $R^3$ may be the same or different and each represents a cyano group, a straight- or branched-chain alkoxycarbonyl group containing from 2 to 6 carbon atoms, or a phenylsulphonyl group which may be unsubstituted or substituted by one or more substituents $R^{10}$ (as hereinbefore defined), $R^1$ represents a group of formula II, $R^4$ and $R^6$ represent hydrogen atoms and m and n both represent 1.

In the present invention when n represents 2 the two halves of the molecule are linked by the components $R^5$ or $R^7$.

Aryl groups and moieties and aroyl groups are, for example, phenyl or benzoyl groups bearing one or more substituents, for example substituents selected from those listed above in the definition of $R^8$ and from groups of the formula $-NR^6CR^4=CR^2R^3$ wherein $R^2$, $R^3$, $R^4$ and $R^6$ are as hereinbefore defined.

The substituents $R^4$ may be the same or different and the substituents $R^6$ may be the same or different.

When $R^2$ and $R^3$ are different, this specification is intended to embrace the E-form and the Z-form, which arise as a result of geometrical isomerism, and mixtures thereof.

Especially important compounds of formula I are as follows:

| | |
|---|---|
| 1,1-bis(phenylsulphonyl)-2-(thiazol-2-ylamino)ethene; | A |
| 1-(5-methyl-1,3,4-thiadiazol-2-ylamino)-2,2-bis(phenylsulphonyl)ethene; | B |
| 1,1-bis(phenylsulphonyl)-2-(1,2,4-triazin-3-ylamino)ethene; | C |
| 1-(benzothiazol-2-ylamino)-2,2-bis(phenylsulphonyl)ethene; | D |
| 1,1-bis(phenylsulphonyl)-2-(quinol-3-ylamino)ethene; | E |
| 1,1-bis(phenylsulphonyl)-2-(pyrazin-2-ylamino)ethene; | F |
| 1,1-bis(phenylsulphonyl)-2-(quinol-2-ylamino)ethene; | G |
| 1-(2,6-dimethylpyrimidin-4-ylamino)-2,2-bis-(phenylsulphonyl)ethene; | H |
| 1-(5-carbamoylpyrazin-2-ylamino)-2,2-bis-(phenylsulphonyl)ethene; | I |
| 1-(4-phenyl-1,2,4-triazol-3-ylamino)-2,2-bis(phenylsulphonyl)ethene; | J |
| 1-benzoyl-2-(5-bromopyrid-2-ylamino)-1-(4-methylphenylsulphonyl)ethene; | K |
| 1-benzoyl-2-(5-bromopyrid-2-ylamino)-1-cyanoethene; | L |
| 2-(5-bromopyrid-2-ylamino)-1-ethoxycarbonyl-1-(4-methylphenylsulphonyl)ethene; | M |
| 2-(5-bromopyrid-2-ylamino)-1-cyano-1-methylsulphonylethene; | N |
| 1-acetyl-2-(5-bromopyrid-2-ylamino)-1-phenylsulphonylethene; | O |
| 2-(5-bromopyrid-2-ylamino)-1-ethylsulphonyl-1-phenylsulphonylethene; | P |
| 2-(5-bromopyrid-2-ylamino)-1,1-bis(methylsulphonyl)ethene; | Q |
| 2-(5-bromopyrid-2-ylamino)-1-ethoxycarbonyl-1-nitroethene; | R |
| 1,1-bis(4-chlorophenylsulphonyl)-2-[2-(trifluoromethyl)anilino]ethene; | S |
| 1,1-bis(4-chlorophenylsulphonyl)-2-(2-cyanoanilino)ethene; | T |
| 1,1-bis(4-chlorophenylsulphonyl)-2-(pyrid-3-ylmethylamino)ethene; | U |
| 2-benzylamino-1,1-bis(4-chlorophenylsulphonyl)ethene; | V |
| 1,1-bis(4-chlorophenylsulphonyl)-2-(pyrid-2-ylmethylamino)ethene; | W |
| 1-phenyl-1-phenylsulphonyl-2-(pyrid-2-ylamino)ethene; | X |
| 2-(5-bromopyrid-2-ylamino)-1-phenyl-1-phenylsulphonylethene; | Y |
| 1-phenylamino-2,2-bis(phenylsulphonyl)ethene; | Z |
| 1-(4-chlorophenylamino)-2,2-bis(phenylsulphonyl)ethene; | AA |
| 1-(3,4-dichlorophenylamino)-2,2-bis(phenylsulphonyl)ethene; | AB |
| 1-(4-methoxyphenylamino)-2,2-bis(phenylsulphonyl)ethene; | AC |
| 1-(4-methylphenylamino)-2,2-bis(phenylsulphonyl)ethene; | AD |
| 1,1-bis(phenylsulphonyl)-2-(pyrimidin-2-ylamino)ethene; | AE |
| 1,1-bis(phenylsulphonyl)-2-(isoquinolin-1-ylamino)ethene; | AF |
| 1-formyl-2-(3-methylpyrid-2-ylamino)ethene; | AG |
| 1-formyl-2-(5-methylpyrid-2-ylamino)ethene; | AH |
| 1-formyl-2-(4,6-dimethylpyrid-2-ylamino)ethene; | AI |
| 1-(5-bromopyrid-2-ylamino)-2-formylethene; | AJ |
| 1-(3,5-dibromopyrid-2-ylamino)-2-formylethene; | AK |
| 2-(purin-6-ylamino)-1,1-bis(ethoxycarbonyl)ethene; | AL |
| 1,1-bis(ethoxycarbonyl)-2-(3-methylpyrid-2-ylamino)ethene; | AM |
| 2,6-bis[2,2-bis(phenylsulphonyl)ethen-1-ylamino]pyridine; | AN |
| 1-[1-(2,3,4-trichlorophenyl)-4-cyanopyrazol-5-yl-amino]-2,2-bis(ethoxycarbonyl)ethene; | AO |
| 2-[2,2-bis(phenylsulphonyl)ethen-1-ylimino]-5-carbamoyl-1-methylpyridine; | AP |
| 1,1-bis(phenylsulphonyl)-2-[N—(5-chloropyrid-2-yl)-N—methylamino]ethene; | AQ |
| 2-[N—(5-chloropyrid-2-yl)-N—methylamino]-1,1-dicyanoethene; | AR |
| 1-(4-methoxyphenylamino)-1-methyl-2-(phenylsulphonyl)ethene; | AS |
| either 1,1-bis(phenylsulphonyl)-2-[N—(5-carbamoylpyrid-2-yl)-N—phenylamino]ethene or 2-[1,1-bis(phenylsulphonyl)ethenylimino]-5-carbamoyl-1-phenyl-1,2-dihydropyridine; | AT |
| 2-[2,2-bis(phenylsulphonyl)ethenylimino]-5-carbamoyl-1-methyl-1,2-dihydropyridine; | AU |
| 5-carbamoyl-2-(2,2-dicyanoethenylamino)pyridine; | AV |
| 2-(2,2-dicyanoethenylamino)-5-(N,N—diethylcarbamoyl)pyridine; | AW |
| 2-[2,2-bis(phenylsulphonyl)ethenylimino]-5-bromo-1-ethyl-1,2-dihydropyridine; | AX |
| 2-[2,2-bis(phenylsulphonyl)ethenylimino]-5-bromo-1-benzyl-1,2-dihydropyridine; | AY |
| 1,1-bis(ethoxycarbonyl)-2-(2,3-dimethyl-3H—imidazo[4,5-b]pyrid-5-ylamino)ethene; | AZ |
| 2-(1-cyano-1-ethoxycarbonylethen-2-yl)-5-(1-cyano-1-ethoxycarbonylethen-2-ylamino)furan; | BA |
| 2,2'-bis[2,2-bis(ethoxycarbonylethenylamino)]-(4,4'-bithiazole); | BB |
| 1,1-bis(ethoxycarbonyl)-2-(3,5-dihydroxyphenylamino)ethene; | BC |
| 1-[N—(5-bromopyrid-2-yl)-N—(4-nitrophenyl)]-amino-2-(4-nitrophenylsulphonyl)ethene; and | BD |
| 1-[N—(5-bromopyrid-2-yl)-N—(4-nitrophenyl)]-amino-2-phenylsulphonylethene. | BE |

Compounds A, C, D, E, G, H, I, L, N, O, R, V, W, X, Z, AG, AH, AI, AJ, AM, AP and BE are of particular importance.

The letters A etc are allocated to the compounds for easy reference later in the specification, e.g. in the Tables and in the Examples.

Especially important classes of compounds of formula I include those in which one or more of the symbols has the following value, the other symbols being as hereinbefore defined:

(i) $R^2$ represents a cyano or formyl group or a straight- or branched-chain alkoxycarbonyl group containing up to 6 carbon atoms, e.g. an ethoxy-carbonyl group, or represents a phenylsulphonyl group optionally carrying at least one substituent, for example a halogen, e.g. chlorine, atom;

(ii) $R^3$ represents a straight- or branched-chain alkoxycarbonyl or alkylsulphonyl group containing up to 6 carbon atoms, e.g. a methylsulphonyl or an ethoxycarbonyl group, or represents a phenylsulphonyl group optionally carrying at least one substituent, for example a halogen, e.g. chlorine, atom, or represents a hydrogen atom, or represents a nitro group or a phenyl or benzoyl group optionally carrying at least one substituent, or represents a straight- or branched-chain alkanoyl group containing up to 6 carbon atoms, eg an acetyl group;

(iii) $R^4$ represents a hydrogen atom;

(iv) $R^5$ represents a thiazolyl, triazinyl, benzothiazolyl, quinolyl, pyrimidinyl, pyrazinyl or pyridinyl group, optionally bearing at least one substituent, e.g. one or two substituents, selected from halogen, e.g. bromine, atoms, carbamoyl groups and alkyl groups of 1 to 6 carbon atoms, e.g. methyl groups, or an optionally substituted phenyl group or an optionally substituted heterocyclylalkyl or arylalkyl group wherein the heterocyclyl or aryl moiety is as hereinbefore defined, e.g. pyridyl or phenyl, and the alkyl moiety is straight or branched and contains 1 or 2 carbon atoms, preferably 1 carbon atom; in general, suitable heterocyclyl, aryl, heterocyclylalkyl and arylalkyl groups are those exemplified in the compounds A to BE;

(v) $R^6$ represents a hydrogen atom or a p-nitrophenyl group;

(vi) $R^7$ represents a pyridylidene group bearing a substituent in the 1-position, e.g. 1-methyl-pyridylidene;

(vii) m represents 1; and/or (viii) n represents 1.

The compounds have valuable pharmacological properties, in particular properties which are indicative of utility in the treatment of arthritic disorders such as rheumatoid arthritis.

For example, from tests in mice it was calculated that compounds of formula I, when twice administered orally, one hour before and four hours after the administration of antigen, each time at the doses shown in the following Table I, would reduce by 50% the inhibition of migration of incubated mouse macrophage cells measured in a manner similar to that described by Likhite et al, Cellular Immunology, Vol 5, 1972, page 377. This is a measure of antagonism or reduction of the levels of lymphokines and is indicative of utility in the treatment of arthritic patients.

TABLE I

| Test Compound | oral ED50 dose (mg/kg animal body weight) |
| --- | --- |
| A | 10 |
| C | 2 |
| H | less than 10 |
| N | 28 |
| O | 14 |
| V | less than 10 |
| W | less than 10 |
| X | 2 |
|   | 10 |
| Z | 2 |
| AG | 10 |
|   | 3.8 |
| AI | 5.2 |
| AP | less than 10 |

TABLE I-continued

| Test Compound | oral ED50 dose (mg/kg animal body weight) |
| --- | --- |
| BE | 4.4 |

Compounds of formula I were also submitted to the delayed-type hypersensitivity (DTH) test, which is an in-vivo model of cellular immunity (Type IV hypersensitivity reaction) which is suppressed by antirheumatic drugs. Previously sensitised mice receive antigen challenge (using methylated bovine serum albumen) by foot pad injection and the resulting foot pad swelling is compared in control animals and animals treated with compounds of formula I.

The results are given in Table II.

TABLE II

| Test Compound | % inhibition | dose mg/kg animal body weight |
| --- | --- | --- |
| E | 38 | 10 |
|   | 15 | 50 |
| D | 27 | 50 |
| G | 30 | 10 |
|   | 24 | 50 |
| I | 30 | 40 |

Furthermore, in laboratory tests, the compounds have been shown to inhibit the deterioration of joints in the limbs of cavies and rats. These results are particularly important because compounds currently employed in the treatment of arthritic disorders are primarily antiinflammatories and do not possess the said ability to inhibit joint deterioration.

The compounds also exhibit properties which are indicative of utility in the treatment of ailments such as allergy, asthma, inflammatory diseases, cerebral ischaemia, myocardial ischaemia and psoriasis.

For example, in tests in vitro at concentrations of 0.0001M, a compound of formula I inhibited lipoxygenase by the percentage shown in the following Table III.

TABLE III

| Test Compound | % inhibition of lipoxygenase |
| --- | --- |
| AM | 62 |

The compounds of formula I also possess valuable immunomodulatory activity and are of use in the treatment of organ grafts and skin grafts and in the treatment of immunological diseases.

The beneficial properties of the compounds of formula I are enhanced by the fact that they have only very low mammalian toxicity.

The compounds of formula I may be prepared by the application or adaptation of known methods, for example as illustrated in the following Examples or as follows.

Thus, as a feature of the present invention, compounds of formula I wherein $R^1$ represents a group of formula II and $R^4$ represents a hydrogen atom ($R^2$, $R^3$, $R^5$, m and n being as hereinbefore defined) are prepared by the reaction of compounds of the general formula:

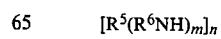

(wherein $R_5$, $R_6$, m and n are as hereinbefore defined) with compounds of the general formula:

$$R^{11}X^1CH=CR^2R^3 \quad \text{IV}$$

(wherein $R^{11}$ represents an alkyl group of 1 to 5 carbon atoms, preferably with a straight chain, e.g. ethyl, $X^1$ represents an oxygen or sulphur atom and $R^2$ and $R^3$ are as hereinbefore defined), generally at temperatures between 0° and 250° C., preferably at or near room temperature or between 80° and 180° C., optionally in the presence of an inert solvent and optionally in the presence of an acid, e.g. hydrochloric acid or ethereal hydrogen chloride, or a catalyst such as 1,5-diazabicyclo[4.3.0]non-5-ene. Suitable inert solvents include aromatic hydrocarbons, e.g. toluene, aliphatic ethers, aliphatic nitriles, aliphatic amides, e.g. dimethylformamide and N,N-dimethylacetamide, sulpholane and, more especially, aliphatic alcohols, e.g. ethanol.

As a further feature of the present invention, compounds of formula I where $R^1$ represents a group of formula II ($R^2$, $R^3$, $R^4$, $R^5$, m and n being as hereinbefore defined) are prepared by the reaction together of compounds of formula III (as hereinbefore defined) and compounds of the general formulae V and VI:

$$R^4C(X^1R^{11})_3 \quad \text{V}$$

$$R^2R^3CH_2 \quad \text{VI}$$

(wherein $R^2$, $R^3$, $R^4$, $R^{11}$ and $X^1$ are as hereinbefore defined), preferably in the absence of a solvent other than an excess of the compound of formula V, and preferably at an elevated temperature, e.g. 120°–150° C.

As a further feature of the present invention compounds of formula I wherein $R_1$ represents an atom =N— and $R^5$ represents a group $R^7$ (as hereinbefore defined) ($R^2$, $R^3$, $R^4$, m and n being as hereinbefore defined) are prepared by the reaction of a salt, preferably an alkali metal, e.g. sodium or potassium, salt of a compound of formula I wherein $R^1$ represents a group of formula II wherein $R^6$ represents a hydrogen atom ($R^2$, $R^3$, $R^4$, $R^5$, m and n being as hereinbefore defined) with an alkylating or arylating agent of the general formula:

$$R^{12}X^2 \quad \text{VII}$$

wherein $R^{12}$ represents a straight- or branched-chain alkyl group containing from 1 to 6 carbon atoms which may be substituted by one or more substitutents $R^8$ or an aryl group which may be substituted by one or more substituents $R^8$ ($R^8$ being as hereinbefore defined) and $X^2$ represents the acid residue of a reactive ester, for example a halogen atom or a toluene-p-sulphonate or methanesulphonate group, or (when $R^{12}$ represents an optionally substituted aryl group $R^{13}$) a group $R^{13}ICl$, preferably in the presence of a solvent such as dimethylformamide and preferably at 20°–150° C.

As a further feature of the present invention compounds of formula I wherein $R^1$ represents a group of formula II, $R_3$ represents a hydrogen atom and $R^6$ represents an aryl group having one or more electron-withdrawing substituents, e.g. nitro groups, for example a phenyl group with one or more nitro groups in its ortho and/or para positions ($R^2$, $R^4$, $R^5$, m and n being as hereinbefore defined) are prepared by the reaction of a compound of formula IV wherein $R^3$ represents an aryl group having one or more said electron-withdrawing substitutents ($R^2$, $R^{11}$ and $X^1$ being as hereinbefore defined) and a compound of the formula III wherein $R^6$ represents a hydrogen atom ($R^5$, m and n being as hereinbefore defined) at an elevated temperature, e.g. 150°–165° C., preferably in a solvent such as N,N-dimethylacetamide.

As a further feature of the present invention compounds of formula I wherein $R^1$ represents a group of formula II, $R^2$ represents a formyl group, $R^3$, $R^4$ and $R^6$ represent hydrogen atoms, $R^5$ represents a pyrid-2-yl group optionally carrying one or more substituents $R^8$ (as hereinbefore defined), and m and n both represent 1, are prepared by the reaction of a compound of the general formula shown in Figure VIII (wherein $R^8$ is as hereinbefore defined, p is 1, 2, 3 or 4 and $X^{3-}$ represents an anion, for example a halide, eg chloride, ion) with a base, for example a mild aqueous alkali, e.g. aqueous sodium bicarbonate, preferably at or near room temperature, e.g. 20°–50° C.

As a further feature of the present invention compounds of formula I wherein $R^1$ represents a group of formula II, $R^2$ represents an optionally substituted arylsulphonyl group, $R^3$ represents a hydrogen atom and $R^4$, $R^5$, $R^6$, m and n are as hereinbefore defined are prepared by the reaction of a compound of formula III (as hereinbefore defined) and a compound of the general formula:

$$R^4C\equiv CR^2 \quad \text{IX}$$

(wherein $R^2$ and $R^4$ are as hereinbefore defined) preferably in a solvent such as an alkanol of 1 to 4 carbon atoms or N,N-dimethylacetamide, at or above room temperature, e.g. at 10°–80° C.

As a further feature of the present invention compounds of formula I wherein $R^1$ represents a group of formula II and $R^3$ represents a group $R^{14}$ within the definition of $R^3$ hereinbefore given but other than a hydrogen atom, $R^2$, $R^4$, $R^6$, m and n being as hereinbefore defined, are prepared by the reaction of an alkali metal salt, e.g. the sodium salt, of a compound of the general formula:

$$R^2R^{14}CH_2 \quad \text{X}$$

(wherein $R^2$ and $R^{14}$ are as hereinbefore defined) with a compound of the general formula:

$$[R^5(NR^6CHR^4X^1R^{11})_m]_n \quad \text{XI}$$

(wherein $R^4$, $R^5$, $R^6$, $R^{11}$, $X^1$, m and n are as hereinbefore defined), optionally at an elevated temperature and in a solvent such as an alkanol of 1 to 4 carbon atoms.

Intermediates of formula VIII may be prepared by the reaction of a compound of formula III, wherein $R^5$ represents a pyrid-2-yl group optionally carrying one or more substituents $R^8$ (as hereinbefore defined), $R^6$ represents a hydrogen atom, and m and n both represent 1, with a compound of the general formula:

$$(R^{11}O)_2CHCH_2CH(OR^{11})_2 \quad \text{XII}$$

(wherein $R^{11}$ is as hereinbefore defined) in dry acidic conditions, e.g. in the presence of anhydrous hydrogen chloride, preferably at an elevated temperature, e.g. 60°–120° C., preferably in a solvent such as an alkanol of 1 to 4 carbon atoms.

By the term "pharmaceutically acceptable salt" in relation to compounds of general formula I is meant a salt formed by reaction with an acid by the application or adaptation of known methods or by reaction with a base by the application or adaptation of known methods so that the anion (in the case of an acid addition salt) or the cation (in the case of a salt formed with a pharmaceutically acceptable base) is relatively innocuous to the animal organism when used in therapeutic doses so that the beneficial pharmacological properties of the parent compound of general formula I are not vitiated by side-effects ascribable to the said anion or cation.

Suitable acid addition salts include salts derived from inorganic acids, for example hydrochlorides, hydrobromides, phosphates, sulphates and nitrates, and organic salts, for example methanesulphonates, 2-hydroxyethanesulphonates, oxalates, lactates, tartrates, acetates, salicylates, citrates, propionates, succinates, fumarates, maleates, methylene-bis-β-hydroxynaphthoates, gentisates and di-p-toluoyltartrates.

Suitable salts formed by compounds of general formula I with pharmaceutically acceptable bases include the alkali metal (e.g. sodium and potassium) alkaline earth metal (e.g. calcium and magnesium), and ammonium salts, and salts of amines known in the art to be pharmaceutically acceptable, e.g. ethylene diamine, choline, diethanolamine, triethanolamine, octadecylamine, diethylamine, triethylamine, 2-amino-2-(hydroxymethyl)propane-1,3-diol and 1-(3,4-dihydroxyphenyl)-2-isopropylaminoethanol.

It is to be understood that, where in this specification reference is made to compounds of general formula I, it is intended to refer also to their pharmaceutically acceptable salts as indicated above, where the context so permits.

Compounds of formulae III, IV, V, VI, VII, IX, X, XI and XII may be prepared by the application or adaptation of known methods.

By the term "known methods" as used in this specification is meant methods heretofore used or described in the literature.

The following Examples illustrate the preparation of the compounds of the present invention.

EXAMPLE 1

Compounds A, B, C, D, E, F, G, H, I and J

A solution of 2-aminothiazole (0.5 g) and 2-ethoxy-1,1-bis(phenylsulphonyl)ethene (1.76 g) in dimethylacetamide (20 ml) was heated at reflux for 3.5 hours. The solution was cooled and poured onto ice (200 g) and then the resulting buff precipitate was filtered off, washed with water and dried in vacuo over phosphorous pentoxide. Recrystallisation from ethyl acetate gave 1,1-bis(phenylsulphonyl)-2-(thiazol-2-ylamino)ethene (0.9 g), m.p. 189°–191° C.

By proceeding in a similar manner, but replacing the 2-aminothiazole, used as a starting material, by the appropriate quantities of:
2-amino-5-methyl-1,3,4-thiadiazole;
3-amino-1,2,4-triazine;
2-aminobenzothiazole;
3-aminoquinoline;
2-aminopyrazine;
2-aminoquinoline;
4-amino-2,6-dimethylpyrimidine;
2-amino-5-carbamoylpyrazine;
3-amino-4-phenyl-1,2,4-triazole;
respectively, there were prepared:
1-(5-methyl-1,3,4-thiadiazol-2-ylamino)-2,2-bis(phenylsulphonyl)ethene, m.p. 203°–205° C. [subjected to medium pressure chromatography on silica gel, eluting with a mixture of chloroform and methanol (50:1 v/v), followed by trituration with light petroleum ether (b.p. 40°–60° C.)];
1,1-bis(phenylsulphonyl)-2-(1,2,4-triazin-3-ylamino)ethene, m.p. 150°–152° C. [subjected to recrystallisation from ethanol followed by medium pressure chromatography on silica gel, eluting with ethyl acetate, then triturated with light petroleum ether (b.p. 40°–60° C.)];
1-(benzothiazol-2-ylamino)-2,2-bis(phenylsulphonyl)ethene, m.p. 182°–183° C. [subjected to medium pressure chromatography on silica gel, eluting with a mixture of chloroform and methanol (125:1 v/v), followed by trituration with ethanol and recrystallisation from a mixture of ethyl acetate and light petroleum ether (b.p 60°–80° C.)];
1,1-bis(phenylsulphonyl)-2-(quinol-3-ylamino)ethene, m.p. 266°–267° C. [purified by trituration with boiling ethanol, followed by recrystallisation from aqueous dimethylformamide];
1,1-bis(phenylsulphonyl)-2-(pyrazin-2-ylamino)ethene, m.p. 167°–169° C. [subjected to medium pressure chromatography on silica gel, eluting with ethyl acetate, followed by trituration with light petroleum ether (b.p. 40°–60° C.)];
1,1-bis(phenylsulphonyl)-2-(quinol-2-ylamino)ethene, m.p. 219°–221° C. [purified by trituration with ethanol followed by recrystallisation from aqueous dimethylformamide];
1-(2,6-dimethylpyrimidin-4-ylamino)-2,2-bis-(phenylsulphonyl)ethene, m.p. 198°–200° C. [subjected to medium pressure chromatography on silica gel, eluting with a mixture of chloroform and methanol (49:1 v/v), followed by trituration with light petroleum ether (b.p. 60°–80° C.), followed by a similar chromatography eluting with ethyl acetate, followed by a similar trituration];
1-(5-carbamoylpyrazin-2-ylamino)-2,2-bis-(phenylsulphonyl)ethene, m.p. 239°–241° C. [purified by recrystallisation from aqueous dimethylformamide followed by trituration with boiling ethyl acetate and diethyl ether];
1-(4-phenyl-1,2,4-triazol-3-ylamino)-2,2-bis(phenylsulphonyl)ethene, approximate m.p. 120°–130° C. [subjected to medium pressure chromatography on silica gel, eluting with ethyl acetate, followed by trituration with light petroleum ether (b.p. 60°–80° C.) and diethyl ether].

EXAMPLE 2

Compounds K, L, M, N, O, P and Q

A solution of 1-benzoyl-2-ethoxy-1-(4-methylphenylsulphonyl)ethene (0.85 g) and 2-amino-5-bromopyridine (0.45 g) in dimethylacetamide (30 ml) was heated at reflux for 2 hours. It was then cooled and poured onto ice (60 g). The resulting off-white precipitate was filtered off, washed with water, dried, and recrystallised from ethyl acetate, to give 1-benzoyl-2-(5-bromopyrid-2-ylamino)-1-(4-methylphenylsulphonyl)ethene (0.4 g), m.p. 205° C.

By proceeding in a similar manner, but replacing the 1-benzoyl-2-ethoxy-1-(4-methylphenylsulphonyl)ethene, used as a starting material, by the appropriate quantities of:
1-benzoyl-1-cyano-2-ethoxyethene;
1-ethoxy-2-ethoxycarbonyl-2-(4-methylphenylsulphonyl)ethene;

1-cyano-2-ethoxy-1-methylsulphonylethene;
1-acetyl-2-ethoxy-1-phenylsulphonylethene;
2-ethoxy-1-ethylsulphonyl-1-phenylsulphonylethene; and
2-ethoxy-1,1-bis(methylsulphonyl)ethene;
respectively, there were prepared:
1-benzoyl-2-(5-bromopyrid-2-ylamino)-1-cyanoethene, m.p. 192° C. (recrystallised from acetone);
2-(5-bromopyrid-2-ylamino)-1-ethoxycarbonyl-1-(4-methylphenylsulphonyl)ethene, m.p. 144°–146° C. [The aqueous suspension was extracted with ethyl acetate, the extract was concentrated to dryness under reduced pressure, and the residual oil was triturated with diethyl ether];
2-(5-bromopyrid-2-ylamino)-1-cyano-1-methylsulphonylethene, m.p. 270°–271° C. [purified by trituration with aqueous hydrochloric acid (2N) and then with water and recrystallised from a mixture of dimethylformamide and methanol];
1-acetyl-2-(5-bromopyrid-2-ylamino)-1-phenylsulphonylethene, m.p. 178° C. (recrystallised from ethanol);
2-(5-bromopyrid-2-ylamino)-1-ethylsulphonyl-1-phenylsulphonylethene, m.p. 164°–165° C. [subjected to medium pressure chromatography on silica gel, eluting with a mixture of chloroform and ethyl acetate (4:1 v/v), followed by recrystallisation from acetone]; and
2-(5-bromopyrid-2-ylamino)-1,1-bis(methylsulphonyl)ethene, m.p. 264°–265° C. (recrystallised from diethyl ether and then from ethyl acetate).

EXAMPLE 3

Compound R

A mixture of 2-ethoxy-1-ethoxycarbonyl-1-nitroethene (5.7 g) and 2-amino-5-bromopyridine (5.2 g) in toluene was heated at reflux with slow removal of the ethanol formed during 2 hours. The reaction mixture was cooled and concentrated in vacuo to give a yellow powder which was triturated with hot ethanol, to give 2-(5-bromopyrid-2-ylamino)-1-ethoxycarbonyl-1-nitroethene (6.0 g) in the form of a pale yellow powder, m.p. 141°–142° C.

EXAMPLE 4

Compounds S, T, U, V and W

A solution of 1,1-bis(4-chlorophenylsulphonyl)-2-ethoxyethene (1.26 g) and 2-(trifluoromethyl)aniline (0.48 g) in dimethylacetamide (20 ml) was heated at reflux for 2 hours, and then it was cooled and poured onto ice (50 g). The resulting white precipitate was filtered off, washed with water and recrystallised from ethanol, to give 1,1-bis(4-chlorophenylsulphonyl)-2-[2-(trifluoromethyl)anilino]ethene (0.8 g), m.p. 169°–171° C.

By proceeding in a similar manner, but replacing the 2-aminobenzotrifluoride, used as a starting material, by the appropriate quantities of:-
2-aminobenzonitrile;
3-(aminomethyl)pyridine;
benzylamine; and
2-(aminomethyl)pyridine;
respectively, there were prepared:
1,1-bis(4-chlorophenylsulphonyl)-2-(2-cyanoanilino)ethene, m.p. 195°–198° C. [recrystallised from ethanol followed by medium pressure chromatography on silica gel, eluting with chloroform, and triturated with light petroleum ether (b.p. 60°–80° C.)];
1,1-bis(4-chlorophenylsulphonyl)-2-(pyrid-3-ylmethylamino)ethene, m.p. 218°–219° C. (recrystallised from a mixture of ethanol and acetone);
2-benzylamino-1,1-bis(4-chlorophenylsulphonyl)ethene, m.p. 211°–212° C. (recrystallised from a mixture of ethanol and acetone); and
1,1-bis(4-chlorophenylsulphonyl)-2-(pyrid-2-ylmethylamino)ethene, m.p. 239°–241° C. (with decomposition) (recrystallised from a mixture of ethanol and acetone).

EXAMPLE 5

Compounds X and Y

A solution of 2-aminopyridine (1.05 g) and 2-methoxy-1-phenyl-1-phenylsulphonylethene (2.0 g) in a mixture of anhydrous dimethylacetamide (50 ml) and a solution of hydrogen chloride in diethyl ether (6N; 0.5 ml) was heated at reflux for 25 hours, and then it was cooled and poured onto ice (150 g). The yellow precipitate was filtered off, subjected twice to medium pressure chromatography on silica gel, eluting with chloroform, triturated with light petroleum ether (b.p. 60°–80° C.) and recrystallised from a mixture of diethyl ether and light petroleum ether (b.p. 60°–80° C.), to give 1-phenyl-1-phenylsulphonyl-2-(pyrid-2-ylamino)ethene (0.3 g), m.p. 159°–160° C.

By proceeding in a similar manner, but replacing the 2-aminopyridine used as starting material by the appropriate quantity of 2-amino-5-bromopyridine, there was prepared:
2-(5-bromopyrid-2-ylamino)-1-phenyl-1-phenylsulphonylethene, m.p. 119°–120° C. [subjected to medium pressure chromatography on silica gel, eluting twice with chloroform, followed by trituration with light petroleum ether (b.p. 60°–80° C.)].

EXAMPLE 6

Compounds Z, AA, AB, AC, AD, AE and AF

A mixture of aniline (1.0 g) and 2-ethoxy-1,1-bis(phenylsulphonyl)ethene (3.5 g) was heated at 160°–180° C. for 30 minutes, allowing any ethanol evolved to escape. After cooling, the residue was recrystallised by dissolving in a minimum of hot choroform and diluting with between 3 and 4 volumes of ethanol to give 1-phenylamino-2,2-bis(phenylsulphonyl)ethene (3.2 g), m.p. 199°–202° C.

By proceeding in a similar manner, but replacing the aniline used as a starting material by the appropriate quantities of:
4-chloroaniline;
3,4-dichloroaniline;
4-methoxyaniline;
4-methylaniline;
2-aminopyrimidine; and
1-aminoisoquinoline;
respectively, there were prepared:
1-(4-chlorophenylamino)-2,2-bis(phenylsulphonyl)ethene, m.p. 172°–174° C. (resolidifies and melts again at 193°–195° C.) (recrystallised from toluene);
1-(3,4-dichlorophenylamino)-2,2-bis(phenylsulphonyl)ethene, m.p. 215°–218° C. (recrystallised from toluene);
1-(4-methoxyphenylamino)-2,2-bis(phenylsulphonyl)ethene, m.p. 184°–186° C. (recrystallised from a mixture of chloroform and ethanol);

1-(4-methylphenylamino)-2,2-bis(phenylsulphonyl)ethene, m.p. 193°–195° C. (recrystallised from a mixture of chloroform and ethanol);

1,1-bis(phenylsulphonyl)-2-(pyrimidin-2-ylamino)ethene, m.p. 165°–166.5° C. (recrystallised from ethanol); and 1,1-bis(phenylsulphonyl)-2-(isoquinolin-1-ylamino)ethene, m.p. 231°–232° C. (recrystallised from a mixture of chloroform and ethanol).

EXAMPLE 7

Compounds AG, AH, AI, AJ and AK

A solution of 2-amino-3-methylpyridine (53.9 g) and anhydrous hydrogen chloride (40 g) in anhydrous ethanol (960 ml) was treated with 1,1,3,3-tetramethoxypropane and heated at reflux for 6 hours. The solution was then concentrated to dryness under reduced pressure and the residue was triturated with diethyl ether, to give crude 9-methylpyrido[1,2-a]pyrimidinium chloride (76 g). This crude salt was dissolved in water (300 ml) and treated with sodium bicarbonate (35.4 g). The mixture was stirred at room temperature for one hour and then it was filtered, washed with water and recrystallised from water, to give 1-formyl-2-(3-methylpyrid-2-ylamino)ethene (32.7 g), m.p. 129°–131° C. (with decomposition).

By proceeding in a similar manner, but substituting for the 2-amino-3-methylpyridine used as a starting material the appropriate quantities of:
2-amino-5-methylpyridine;
2-amino-4,6-dimethylpyridine;
2-amino-5-bromopyridine;
2-amino-3,5-dibromopyridine;
respectively, there were prepared:
1-formyl-2-(5-methylpyrid-2-ylamino)ethene, m.p. 178°–180° C. (with decomposition) (recrystallised from water);
1-formyl-2-(4,6-dimethylpyrid-2-ylamino)ethene, m.p. 163°–165° C. (with decomposition (recrystallised from aqueous ethanol);
1-(5-bromopyrid-2-ylamino)-2-formylethene, m.p. 190° C. (with decomposition) (recrystallised from ethanol); and
1-(3,5-dibromopyrid-2-ylamino)-2-formylethene, m.p. 180°–182° C. (with decomposition) (recrystallised from aqueous dimethylformamide).

EXAMPLE 8

Compound AL

A mixture of 6-aminopurine (13.5 g), triethylamine (10.1 g) and 2-ethoxy-1,1-bis(ethoxycarbonyl)ethene (21.6 g) in dimethylformamide (100 ml) was heated at reflux for 16 hours. It was then cooled and the product which separated was crystallised from dimethylformamide and washed with diethyl ether, to give 2-(purin-6-ylamino)-1,1-bis(ethoxycarbonyl)ethene (23 g), in the form of colourless, fluffy crystals, m.p. 234° C. (with decomposition).

EXAMPLE 9

Compound AM

A mixture of 2-amino-3-methylpyridine (5.5 g) and 2-ethoxy-1,1-bis(ethoxycarbonyl)ethene (10.8 g) was heated in a heating bath at 135° C. for 30 minutes. It was then cooled and triturated with light petroleum ether (b.p. 40°–60° C.). The resulting crude solid was recrystallised from light petroleum ether (b.p. 40°–60° C.), to give 1,1-bis(ethoxycarbonyl)-2-(3-methylpyrid-2-ylamino)ethene (10.3 g), m.p. 65°–67° C.

EXAMPLE 10

Compound AN

A stirred mixture of 2,6-diaminopyridine (0.3 g) and 2-ethoxy-1,1-bis(phenylsulphonyl)ethene (2.1 g) in toluene (50 ml) was heated at reflux for 2 hours. The mixture was cooled, and concentrated in vacuo, and the resulting solid was subjected to medium pressure chromatography on silica gel, eluting with acetone, to give 2,6-bis[2,2-bis(phenylsulphonyl)ethen-1-ylamino]pyridine (0.45 g), in the form of a white powder, m.p. 299°–300° C.

EXAMPLE 11

Compound AO

A solution of sodium (0.46 g) in anhydrous ethanol (30 ml) was treated successively with diethyl malonate (1.7 g) and with 1-(2,3,4-trichlorophenyl)-4-cyano-5-(2-ethoxymethyleneimino)pyrazole (3.4 g) and then the mixture was heated at reflux for one hour. The mixture was then cooled and neutralised by treatment with aqueous acetic acid (1N). The resulting pale yellow precipitate was filtered off, washed with ethanol, and recrystallised from a mixture of ethyl acetate and hexane, to give 1-[1-(2,3,4-trichlorophenyl)-4-cyanopyrazol-5-ylamino]-2,2-bis(ethoxycarbonyl)ethene (2.7 g), m.p. 157°–158° C.

EXAMPLE 12

A mixture of 2-(5-carbamoylpyrid-2-ylamino)-1,1-bis(phenylsulponyl)ethene (0.2 g); and aqueous sodium hydroxide (2N; 10 ml) was stirred at room temperature for 24 hours. The resulting solid was filtered off and washed with a small quantity of water, to give the dihydrate of the sodium salt of the starting material (0.19 g), m.p. 288°–289° C. (with decomposition). It was then dried at 100° C./14 mmHg. The resulting anhydrous sodium salt of the starting material was dissolved in dry dimethylformamide (10 ml), treated with iodomethane (0.2 ml), stirred at room temperature for 8 hours and left to stand overnight. The solution was evaporated in vacuo and the residue was triturated with water and recrystallised from aqueous dimethylformamide, to give 2-[2,2-bis(phenylsulphonyl)ethen-1-ylimino]-5-carbamoyl-1-methylpyridine (0.17 g), m.p. 263°–264° C. (with decomposition).

EXAMPLE 13

Compound AQ

A mixture of 5-chloro-2-(methylamino)pyridine (0.41 g), 2-ethoxy-1,1-bis(phenylsulphonyl)ethene and concentrated hydrochloric acid (1 drop) in toluene (20 ml) was heated at reflux for 4 hours and then the mixture was treated with 1,5-diazabicyclo[4.3.0]-non-5-ene (3 drops) and heated at reflux for 18 hours. The reaction mixture was cooled and concentrated in vacuo to give an oil which was triturated with ethanol to give a brown solid which was recrystallised from toluene to give 1,1-bis(phenylsulphonyl)-2-[N-(5-chloropyrid-2-yl)-N-methylamino]ethene (0.2 g), mp. 205°–206° C.

By proceeding in a similar manner but omitting the hydrochloric acid, the same compound (0.37 g) was obtained in a crude form.

EXAMPLE 14

Compound AR

A stirred mixture of 5-chloro-2-(methylamino)pyridine (2.4 g) and ethoxymethylenemalonitrile (2.14 g) was heated at 110° C. for 30 minutes. The mixture was then cooled and subjected to medium pressure chromatography on a short column of silica gel using chloroform as the eluent, to give 2-[N-(5-chloropyrid-2-yl)-N-methylamino]-1,1-dicyanoethene (1.17 g), m.p. 136°–137° C.

EXAMPLE 15

Compound AS

A stirred solution of 1-phenylsulphonylpropyne (0.25 g) in anhydrous methanol (10 ml) was treated with 4-anisidine (0.17 g) and the homogeneous mixture was allowed to stand at room temperature overnight. The methanol was removed in vacuo to give 1-(4-methoxyphenylamino)-1-methyl-2-(phenylsulphonyl)ethene (0.4 g) in the form of a dark brown oil [NMR (in deuterated dimethylsulphoxide: 2.16, 3.76, 7.04, 7.62, 7.84, 8.68 ppm].

EXAMPLE 16

Compound AT

A stirred solution of 1,1-bis(phenylsulphonyl)-2-(5-carbamoylpyrid-2-ylamino)ethene (0.44 g) in dried dimethylformamide (10 ml) was treated with sodium hydride (0.024 g), and after hydrogen evolution had ceased, diphenyliodonium chloride (0.33 g). The mixture was stirred overnight, and was then concentrated in vacuo to give a brown oil, which solidified upon trituration with water, to give a pale yellow solid (0.25 g). The melting point of a sample, after recrystallisation from water, was 181°–182° C. (with decomposition) and the structure was either 1,1-bis(phenylsulphonyl)-2-[N-(5-carbamoyl-pyrid-2-yl)-N-phenylamino]ethene or 2-[1,1-bis(phenylsulphonyl)ethenylimino]-5-carbamoyl-1-phenyl-1,2-dihydropyridine.

EXAMPLE 17

Compound AU

A solution of the sodium salt of 1,1-bis(phenylsulphonyl)-2-(5-carbamoylpyrid-2-ylamino)ethene (0.4 g) in dry dimethylformamide (10 ml) was treated with an excess of methyl iodide (0.46 g). The mixture, which slowly produced some solid material, was stirred at room temperature for 8 hours and was then allowed to stand for 2 days. The solution (which was now clear) was evaporated to dryness at below 40° C. under high vacuum and the resulting residue in the form of a yellow syrup was treated with water (10 ml) to give a cream solid (0.33 g), m.p. 252°–256° C. (with decomposition). Recrystallisation from aqueous dimethylformamide (1:2 v/v; 12 ml) gave 2-[2,2-bis(phenylsulphonyl)ethenylimino]-5-carbamoyl-1-methyl-1,2-dihydropyridine (0.17 g), m.p. 263°–264° C. (with decomposition).

EXAMPLE 18

Compound AV

6-Aminonicotinamide (0.69 g), ethoxymethylenemalononitrile (0.61 g) and N,N-dimethylacetamide (20 ml) were stirred together at room temperature for 10 hours and then allowed to stand for 2 days. The mixture was then evaporated to dryness at below 35° C. under high vacuum and the residue was triturated with water to give a buff solid (0.75 g), m.p. 230°–235° C. (with decomposition). This was triturated with pure acetone (30 ml) and the insoluble residue (0.68 g) was filtered off, dried and dissolved in a minimum of dry dimethylformamide by warming to 60° C. Silica gel, deactivated by treatment with water (20% w/w; 5 g) was added, and the mixture was evaporated at below 35° C. under high vacuum, and the resulting solid was added to a short column of silica gel and eluted under medium pressure with mixtures of ethyl acetate (9:1 v/v and then 2:1 v/v). A small fraction was collected and evaporated and the residue was triturated with a mixture of diethyl ether and light petroleum (b.p. 40°–60° C.) (1:2 v/v) and then with diethyl ether, to give 5-carbamoyl-2-(2,2-dicyanoethenylamino)pyridine (0.1 g), m.p. 215°–218° C. (with decomposition.

Further quantities (totalling 0.25 g) of less pure product were obtained from other fractions eluted from the column.

EXAMPLE 19

Compound AW

A mixture of 2-amino-5-(diethylcarbamoyl)pyridine (0.48 g) and ethoxymethylenemalononitrile (0.31 g) in dry N,N-dimethylacetamide (15 ml) was stirred at room temperature for 24 hours and then allowed to stand for 2 days. The mixture was evaporated to dryness at less than 35° C. under high vacuum, and the residue was triturated with water (20 ml) to give a pinkish solid (0.57 g), m.p. 225°–232° C. (with decomposition). This solid was dissolved in methanol (150 ml), and treated with silica gel deactivated by treatment with water (20% w/w; 6 g). The mixture wws evaporated to dryness under reduced pressure, and the residue was added to a short column of silica gel and eluted under medium pressure with a mixture of ethyl acetate and methanol (4:1 v/v), to give 2-(2,2-dicyanoethenylamino)-5-(N,N-diethylcarbamoyl)pyridine (0.5 g), m.p. 226°–227° C. (with decomposition).

EXAMPLE 20

Compound AX

A solution of 2-[2,2-bis(phenylsulphonyl)ethenylamino]-5-bromopyridine (3.19 g) in dry N,N-dimethylacetamide (30 ml) was treated with crystalline sodium hydride (0.16 g), and the mixture was stirred and heated in an oil bath at 80° C. for 20 hours. Ethyl iodide (2.93 g) was then added to the mixture which was stirred and heated under reflux at 80° C., with occasional shaking, for 24 hours. The mixture was then evaporated at below 40° C. under high vacuum to give a yellow-orange syrup, which was treated with ice-water (30 ml) to give a yellow solid (3.26 g), m.p. 208°–218° C. Recrystallisation from 2-ethoxyethanol gave 2-[2,2-bis(phenylsulphonyl)ethenylimino]-5-bromo-1-ethyl-1,2-dihydropyridine (2.22 g), m.p. 233°–235° C.

EXAMPLE 21

Compound AY

By proceeding in a manner similar to that described in Example 20, but replacing the ethyl iodide by the appropriate quantity of benzyl bromide, there was obtained 2-[2,2-bis(phenylsulphonyl)ethenylimino]-5-bromo-1-benzyl-1,2-dihydropyridine, m.p. 216°–217° C.

EXAMPLE 22

Compound AZ

A solution of 5-amino-2,3-dimethyl-3H-imidazo-[4,5-b]pyridine (4.86 g) and 2-ethoxy-1,1-bis-(ethoxycarbonyl)ethene (7.13 g) in toluene (200 ml) was stirred and heated at reflux for 2 hours and then it was evaporated to dryness. The residue was extracted 3 times with boiling petroleum ether (b.p. 80°–100° C.), the extracts were filtered while hot and the filtrate was then cooled to 0° C. The resulting yellow solid was filtered off, to give 1,1-bis(ethoxycarbonyl)-2-(2,3-dimethyl-3H-imidazo-[4,5-b]pyrid-5-ylamino)ethene (8.4 g) in the form of a yellow sold, m.p. 128°–130° C.

EXAMPLE 23

Compound BA

A mixture of 2-nitrofuran (6.8 g) and a catalyst of palladium on charcoal (5% w/w; 2.72 g) in dioxan (200 ml) was hydrogenated at ambient temperature and atmospheric pressure until 3 equivalents of hydrogen had been absorbed. The mixture was filtered and the filtrate was treated with a solution of 2-ethoxy-1,1-bis(ethoxycarbonyl)ethene (10.14 g) in dioxan (100 ml). The resulting solution was kept at ambient temperature overnight and then it was evaporated to dryness to give a solid, which was washed with a small volume of chloroform and subjected to medium pressure chromatography on silica gel, eluting with chloroform, then a similar medium pressure chromatography on silica gel but eluting with ethyl acetate. Recrystallisation from ethyl acetate gave 2-(1-cyano-1-ethoxycarbonylethen-2-yl)-5-(1-cyano-1-ethoxycarbonylethen-2-ylamino)furan (2.0 g), in the form of orange-yellow needles, m.p. 206°–208° C.

EXAMPLE 24

Compound BB

A mixture of (4,4'-bithiazole)-2,2'-diamine (100 mg) and 2-ethoxy-1,1-bis(ethoxycarbonyl)ethene (6.6 g) was heated at 110° C. for 105 minutes, and then it was cooled and diluted with diethyl ether. The resulting solid was recrystallised from acetone, to give 2,2'-bis[2,2-bis(ethoxycarbonylethenylamino)](4,4'-bithiazole) (0.4 g), m.p. 223°–224° C.

EXAMPLE 25

Compound BC

A mixture of 3,5-dihydroxyaniline (2.0 g), 2-ethoxy-1,1-bis(ethoxycarbonyl)ethene (3.0 g) and ethanol (10 ml) was left to stand at room temperature for 2 days. The resulting solid was filtered off, dissolved in dimethylsulphoxide (20 ml) and then treated with water (100 ml). The resulting solid was washed with water, to give 1,1-bis(ethoxycarbonyl)-2-(3,5-dihydroxyphenylamino)ethene (3.2 g), m.p. 190°–192° C.

EXAMPLE 26

Compound BD

A solution of 2-ethoxy-1,1-bis(4-nitrophenylsulphonyl)ethene (2.55 g) and 2-amino-5-bromopyridine (1.0 g) in anhydrous dimethylacetamide (25 ml) was heated at reflux for 2 hours, and then it was cooled and poured onto ice (150 g). The mixture was extracted with ethyl acetate and the organic layer was dried over magnesium sulphate and evaporated to dryness under reduced pressure. The residue was triturated with diethyl ether and then with a mixture of ethyl acetate and chloroform (100 ml; 1:1 v/v). Recrystallisation of the solid from a mixture of dimethylformamide and methanol gave 1-[N-(5-bromopyrid-2-yl)-N-(4-nitrophenyl)-]amino-2-(4-nitrophenylsulphonyl)ethene (0.5 g), m.p. 235°–236° C.

EXAMPLE 27

Compound BE

A mixture of 2-ethoxy-1-(4-nitrophenylsulphonyl)-1-phenylsulphonylethene (1.6 g) and 2-amino-5-bromopyridine (0.7 g) in N-N-dimethylacetamide (10 ml) was heated at reflux for 3.5 hours, and then it was cooled and poured onto ice. The resulting solid was removed by filtration and subject to medium pressure chromatography on a column of silica gel, eluting with a mixture of chloroform and ethyl acetate (4:1 v/v), followed by recrystallisation from ethanol, to give 1-[N-(5-bromopyrid-2-yl)-N-(4-nitrophenyl)]amino-2-phenylsulphonylethene (0.35 g) in the form of a yellow powder. m.p. 195°–198° C.

EXAMPLE 28

Compounds BF to HV

By proceeding in a manner similar to that described in one or more of the foregoing Examples, there were prepared:

| | |
|---|---|
| 1-formyl-2-(4-pyridylamino)ethene, m.p. 216–217° C. (with decomposition), | BF |
| 1-formyl-2-(3-pyridylamino)ethene, m.p. 164–165° C., | BG |
| 1-formyl-2-(anilino)ethene, m.p. 119–121° C., | BH |
| 2,4-bis[2,2-bis(ethoxycarbonyl)ethen-1-ylamino]-toluene, | BI |
| 1,4-bis[2,2-bis(ethoxycarbonyl)ethen-1-ylamino]benzene, m.p. 164–164.5° C., | BJ |
| 4,6-bis[2,2-bis(ethoxycarbonyl)ethen-1-ylamino]-2-methylquinoline, m.p. 152–153° C., | BK |
| 2,6-bis[2,2-bis(ethoxycarbonyl)ethen-1-ylamino]-pyridine, m.p. 135–136° C., | BL |
| 2-(3-ethoxy-4-decyloxyanilino)-1-ethoxycarbonyl-1-nitroethene, m.p. 68–70° C., | BM |
| 1-cyano-1-phenyl-2-(5-bromopyrid-2-ylamino)ethene, 1-cyano-1-ethoxycarbonyl-2-[ m.p. 219–221° C., | |
| 1-cyanol-1-ethoxycarbonyl-2-[2-tert-butyl-4,5-bis(methoxycarbonyl)anilino]ethene, m.p. 165–167° C., | BO |
| 1-cyano-1-ethoxycarbonyl-2-(2,6-dimethylanilino)ethene, m.p. 165–167° C., | BP |
| 1,1-dicyano-2-(4-methylpyrid-3-ylamino)ethene, m.p. 217–219° C., | BQ |
| 1,1-dicyano-2-(4,6-dimethylpyrid-2-ylamino)ethene, m.p. 201–202° C., | BR |
| 1,1-dicyano-2-(6-methylpyrid-2-ylamino)ethene, m.p. 183–185° C., | BS |
| 1,1-dicyano-2-(6-benzylpyrid-2-ylamino)ethene, m.p. 212–215° C., | BT |
| 1,1-dicyano-2-(2,6-dimethylanilino)ethene, m.p. 171–173° C., | BU |
| 2-(3-ethoxy-4-decyloxyanilino)-2-ethoxycarbonyl-1-acetylethene, m.p. 58–59° C., | BV |
| 1-acetyl-1-ethoxycarbonyl-2-(2,6-dimethylanilino)-ethene, m.p. 73–75° C., | BW |
| 1,1-bis(ethoxycarbonyl)-2-(3-methylisothiazol-5-ylamino)ethene, m.p. 78–79° C., | BX |
| 1,1-bis(ethoxycarbonyl)-2-(quinol-2-ylamino)ethene, m.p. 109–110° C., | BY |
| 1,1-bis(ethoxycarbonyl)-2-(2-methylquinol-4-ylamino)-ethene, m.p. 110–111° C., | BZ |
| 1,1-bis(ethoxycarbonyl)-2-(3-methylisothiazol-4-yl-amino)ethene, m.p. 76–78° C., | CA |
| 1,1-bis(ethoxycarbonyl)-2-(2-phenylquinol-4-yl-amino)ethene, m.p. 129–130° C., | CB |
| 1,1-bis(ethoxycarbonyl)-2-(isothiazol-3-ylamino)ethene, | CC |

| Compound | Code |
|---|---|
| m.p. 129–130° C., | |
| 1,1-bis(ethoxycarbonyl)-2-(isothiazol-4-ylamino)ethene, m.p. 118–119° C., | CD |
| 1,1-bis(ethoxycarbonyl)-2-(2-hydroxyanilino)ethene, m.p. 141–142° C., | CE |
| 2-(3-ethoxy-4-decyloxyanilino)-1,1-bis(ethoxycarbonyl)ethene, m.p. 47° C., | CF |
| 2-(4-chloroanilino)-1,1-bis(ethoxycarbonyl)ethene, m.p. 80–81° C., | CG |
| 2-(4-nitroanilino)-1,1-bis(ethoxycarbonyl)ethene, m.p. 142–142.5° C., | CH |
| 2-(4-carboxyanilino)-1,1-bis(ethoxycarbonyl)ethene, m.p. 224–225° C., | CI |
| 2-(4-aminoanilino)-1,1-bis(ethoxycarbonyl)ethene, m.p. 118–119° C., | CJ |
| 2-(2-nitropyrid-3-ylamino)-1,1-bis(ethoxycarbonyl)ethene, m.p. 139–140° C., | CK |
| 2-(2-chloropyrid-3-ylamino)-1,1-bis(ethoxycarbonyl)ethene, m.p. 79–81° C., | CL |
| 2-(4,6-dimethylpyrid-2-ylamino)-1,1-bis(ethoxycarbonyl)ethene, m.p. 98–101° C., | CM |
| 2-(1,3-dioxoisoindol-2-ylamino)-1,1-bis(ethoxycarbonyl)ethene, m.p. 153–156° C., | CN |
| 2-(3,5-dinitroanilino)-1,1-bis(ethoxycarbonyl)ethene, m.p. 154–155° C., | CO |
| 2-(3-nitro-4-aminoanilino)-1,1-bis(ethoxycarbonyl)ethene, m.p. 186–188° C., | CP |
| 2-(2-nitroanilino)-1,1-bis(ethoxycarbonyl)ethene, m.p. 107–109° C., | CQ |
| 2-(4-isopropylpiperazin-1-ylamino)-1,1-bis-(ethoxycarbonyl)ethene, m.p. 178–180° C. (with decomposition) | CR |
| 2-(8-hydroxyquinol-5-ylamino)-1,1-bis(ethoxycarbonyl)ethene, m.p. 164–166° C., | CS |
| 2-(8-ethoxyquinol-5-ylamino)-1,1-bis(ethoxycarbonyl)ethene, m.p. 92–94° C., | CT |
| 2-(2-hydroxy-4-nitroanilino)-1,1-bis(ethoxycarbonyl)ethene, m.p. 232–234° C., | CU |
| 2-(2-hydroxy-5-nitroanilino)-1,1-bis(ethoxycarbonyl)ethene, m.p. 224–226° C., | CV |
| 2-(4-hydroxy-3-nitroanilino)-1,1-bis(ethoxycarbonyl)ethene, m.p. 147–149° C., | CW |
| 2-(2-hydroxypyrid-3-ylamino)-1,1-bis(ethoxycarbonyl)ethene, m.p. 203–204.5° C., | CX |
| 2-(4-hydroxy-3-carboxyanilino)-1,1-bis(ethoxycarbonyl)ethene, m.p. 165–166° C., | CY |
| 2-(2-hydroxy-5-carboxyanilino)-1,1-bis-(ethoxycarbonyl)ethene, m.p. 235–237° C. (with decomposition) | CZ |
| 2-(3-hydroxypyridyl-2-amino)-1,1-bis(ethoxycarbonyl)ethene, m.p. 187–188.5° C., | DA |
| 1,1-bis(ethoxycarbonyl)-2-[4(5)-carbamoyltriazol-5(4)-ylamino]ethene, m.p. 233–235° C. (with decomposition) | DB |
| 2-[4-hydroxy-3-(tetrazol-5-yl)carbamoylanilino]-1,1-bis(ethoxycarbonyl)ethene, m.p. 268–270° C. (with decomposition) | DC |
| 2-(2,4-dichloroanilino)-1,1-bis(ethoxycarbonyl)ethene, m.p. 112–114° C., | DD |
| 2-(2,5-dichloroanilino)-1,1-bis(ethoxycarbonyl)ethene, m.p. 118–120° C., | DE |
| 2-(3,5-dichloroanilino)-1,1-bis(ethoxycarbonyl)ethene, m.p. 89–91° C., | DF |
| 2-(3,4-dichloroanilino)-1,1-bis(ethoxycarbonyl)ethene, m.p. 79–81° C., | DG |
| 2-(2,3-dichloroanilino)-1,1-bis(ethoxycarbonyl)ethene, m.p. 99–101° C., | DH |
| 2-(2,6-dichloroanilino)-1,1-bis(ethoxycarbonyl)ethene, m.p. 82–85° C., | DI |
| 2-(3-chloroanilino)-1,1-bis(ethoxycarbonyl)ethene, m.p. 55–57° C., | DJ |
| 2-(2-chloroanilino)-1,1-bis(ethoxycarbonyl)ethene, m.p. 92–94° C., | DK |
| 2-(3-nitroanilino)-1,1-bis(ethoxycarbonyl)ethene, m.p. 82–84° C., | DL |
| 2-(3-trifluoromethylanilino)-1,1-bis(ethoxycarbonyl)ethene, m.p. 45–47° C., | DM |
| 2-(2-trifluoromethylanilino)-1,1-bis(ethoxycarbonyl)ethene, m.p. 90–92° C., | DN |
| 2-anilino-1,1-bis(ethoxycarbonyl)ethene, m.p. 47–48° C., | DO |
| 2-(3,5-dimethylanilino)-1,1-bis(ethoxycarbonyl)ethene, m.p. 89–91° C., | DP |
| 2-(2,5-dimethylanilino)-1,1-bis(ethoxycarbonyl)ethene, m.p. 63–64° C., | DQ |
| 2-(2,6-dimethylanilino)-1,1-bis(ethoxycarbonyl)ethene, m.p. 66–68° C., | DR |
| 2-(2-chloro-5-methylanilino)-1,1-bis(ethoxycarbonyl)ethene, m.p. 91–92° C., | DS |
| 2-(3-chloro-2-methylanilino)-1,1-bis(ethoxycarbonyl)ethene, m.p. 79–80° C., | DT |
| 2-(3-chloro-4-methylanilino)-1,1-bis(ethoxycarbonyl)ethene, m.p. 72–74° C., | DU |
| 2-(5-chloro-2-methylanilino)-1,1-bis(ethoxycarbonyl)ethene, m.p. 94–96° C., | DV |
| 2-(4-chloro-2-methylanilino)-1,1-bis(ethoxycarbonyl)ethene, m.p. 88–90° C., | DW |
| 2-(2-chloro-6-methylanilino)-1,1-bis(ethoxycarbonyl)ethene, m.p. 75–77° C., | DX |
| 2-(2-chloro-4-methylanilino)-1,1-bis(ethoxycarbonyl)ethene, m.p. 101–103° C., | DY |
| 2-(3-fluoroanilino)-1,1-bis(ethoxycarbonyl)ethene, m.p. 45–47° C., | DZ |
| 2-(2-fluoroanilino)-1,1-bis(ethoxycarbonyl)ethene, m.p. 81–82° C., | EA |
| 2-(4-fluoroanilino)-1,1-bis(ethoxycarbonyl)ethene, m.p. 69–71° C., | EB |
| 2-(2,4,5-trichloroanilino)-1,1-bis(ethoxycarbonyl)ethene, m.p. 114–116° C., | EC |
| 2-(2-nitro-4-chloroanilino)-1,1-bis(ethoxycarbonyl)ethene m.p. 110–115° C., | ED |
| 2-(4-nitro-2-chloroanilino)-1,1-bis(ethoxycarbonyl)ethene m.p. 136–138° C., | EE |
| 2-(4-benzoylanilino)-1,1-bis(ethoxycarbonyl)ethene, m.p. 43–46° C., | EF |
| 2-(4-nitro-2-trifluoromethylanilino)-1,1-bis-(ethoxycarbonyl)ethene, m.p. 113–115° C., | EG |
| 2-(4-benzyloxyanilino)-1,1-bis(ethoxycarbonyl)ethene, m.p. 112–114° C., | EH |
| 2-[4-(4-m-tolylphenoxy)anilino]-1,1-bis(ethoxycarbonyl)ethene, m.p. 49–51° C., | EI |
| 2-(2,6-diethylanilino)-1,1-bis(ethoxycarbonyl)ethene, m.p. 79–81° C., | EJ |
| 2-(4-cyanoanilino)-1,1-bis(ethoxycarbonyl)ethene, m.p. 112–114° C., | EK |
| 2-(2,4-dimethyl-6-nitroanilino)-1,1-bis(ethoxycarbonyl)ethene, m.p. 109–111° C., | EL |
| 2-(2,4,6-trimethylanilino)-1,1-bis(ethoxycarbonyl)ethene, m.p. 87–89° C., | EM |
| 2-(2-ethylanilino)-1,1-bis(ethoxycarbonyl)ethene, m.p. 43–45° C., | EN |
| 2-(2,6-dibromoanilino)-1,1-bis(ethoxycarbonyl)ethene, m.p. 72–74° C., | EO |
| 2-(2-methoxy-5-nitroanilino)-1,1-bis(ethoxycarbonyl)ethene, m.p. 153–155° C., | EP |
| 2-(6-nitro-1,3-benzo[d]dioxole-5-amino)-1,1-bis(ethoxycarbonyl)ethene, m.p. 167–169° C., | EQ |
| 2-(3,4-diethoxyanilino)-1,1-bis(ethoxycarbonyl)ethene, m.p. 64–66° C., | ER |
| 2-(2-ethoxyanilino)-1,1-bis(ethoxycarbonyl)ethene, m.p. 65–67° C., | ES |
| 2-(3-ethoxyanilino)-1,1-bis(ethoxycarbonyl)ethene, m.p. 34–36° C., | ET |
| 2-(4-ethoxyanilino)-1,1-bis(ethoxycarbonyl)ethene, m.p. 55–56° C., | EU |
| 2-(2-carboxyanilino)-1,1-bis(ethoxycarbonyl)ethene, m.p. 159–161° C., | EV |
| 2-(2-methoxycarbonylanilino)-1,1-bis(ethoxycarbonyl)ethene, m.p. 57–58° C., | EW |
| 2-(3-octyloxyanilino)-1,1-bis(ethoxycarbonyl)ethene, m.p. 34–35° C., | EX |
| 2-(4-bromo-2-methylanilino)-1,1-bis(ethoxycarbonyl)ethene m.p. 103–105° C., | EY |
| 2-(2-bromo-4-nitroanilino)-1,1-bis(ethoxycarbonyl)ethene, m.p. 140–142° C., | EZ |
| 2-(3-hexyloxyanilino)-1,1-bis(ethoxycarbonyl)ethene, m.p. below 20° C., | FA |
| 2-(4-hexyloxyanilino)-1,1-bis(ethoxycarbonyl)ethene, m.p. 39–41° C., | FB |
| 2-(4-octyloxy-3-methoxyanilino)-1,1-bis(ethoxycarbonyl)ethene, m.p. 49–52° C., | FC |
| 2-(4-heptyloxy-3-methoxyanilino)-1,1-bis(ethoxycarbonyl)ethene, m.p. 36–38° C., | FD |
| 2-(4-decyloxyanilino)-1,1-bis(ethoxycarbonyl)-ethene, | FE |

| | |
|---|---|
| m.p. 41-43° C., | |
| 2-(3,4-dibromoanilino)-1,1-bis(ethoxycarbonyl)ethene, m.p. 87-89° C., | FG |
| 2-(2,5-dibromoanilino)-1,1-bis(ethoxycarbonyl)ethene, m.p. 122-124° C., | FH |
| 2-(2,4-dibromoanilino)-1,1-bis(ethoxycarbonyl)ethene, m.p. 135-137° C., | FI |
| 2-(4-nonyloxy-3-methoxyanilino)-1,1-bis(ethoxycarbonyl)ethene, red oil, | FJ |
| 2-(3-bromo-4-tert-butylanilino)-1,1-bis(ethoxycarbonyl)ethene, m.p. 82-85° C., | FK |
| 2-(2-iodo-4-nitroanilino)-1,1-bis(ethoxycarbonyl)ethene, m.p. 152-153° C., | FL |
| 2-(2-aminoanilino)-1,1-bis(ethoxycarbonyl)ethene, m.p. 90-91° C., | FM |
| 7-[2,2-bis(ethoxycarbonyl)ethen-1-ylamino]-5-methyltetrazoloquinoline, m.p. 205-206° C., | FN |
| 2-(2-pyridylamino)-1,1-bis(ethoxycarbonyl)ethene, m.p. 67-68° C., | FO |
| 2-(3-pyridylamino)-1,1-bis(ethoxycarbonyl)ethene, m.p. 60-61° C., | FP |
| 2-(6-purinylamino)-1,1-bis(ethoxycarbonyl)ethene, m.p. 234° C., | FQ |
| 2-[1-(2,3,5,6-tetrafluoro-4-ethylphenyl)-4-cyanopyrazol-5-ylamino]-1,1-bis(ethoxycarbonyl)ethene, m.p. 98-100° C., | FR |
| 2-[1-(2,6-dichloro-4-trifluoromethylphenyl)-3-methyl-4-cyanopyrazol-5-ylamino]-1,1-bis(ethoxycarbonyl)ethene, m.p. 106-108° C., | FS |
| 2-[1-(2,6-dichloro-4-trifluoromethylphenyl)-4-cyanopyrazol-5-ylamino]-1,1-bis(ethoxycarbonyl)ethene, m.p. 118-119° C., | FT |
| 2-(2-chloro-5-nitroanilino)-1,1-bis(ethoxycarbonyl)ethene m.p. 117-118° C., | FU |
| 2-(3,4-dimethoxybenzylamino)-1,1-bis(ethoxycarbonyl)ethene, m.p. 57-60° C., | FV |
| 2-(2-methylbenzylamino)-1,1-bis(ethoxycarbonyl)ethene, m.p. 81-83° C., | FW |
| 2-benzylamino-1,1-bis(ethoxycarbonyl)ethene, m.p. 70-72° C., | FX |
| 2-(4-hydroxy-3-methoxyanilino)-1,1-bis(ethoxycarbonyl)ethene, m.p. 101-102° C., | FY |
| 2-(4-methoxyanilino)-1,1-bis(ethoxycarbonyl)ethene, m.p. 36-38° C., | FZ |
| 2-(3-methylanilino)-1,1-bis(ethoxycarbonyl)ethene, m.p. 41-43° C., | GA |
| 2-(2-methylanilino)-1,1-bis(ethoxycarbonyl)ethene, m.p. 65-67° C., | GB |
| 2-(4-methylanilino)-1,1-bis(ethoxycarbonyl)ethene, m.p. 47-49° C., | GC |
| 2-(3,4-dimethylanilino)-1,1-bis(ethoxycarbonyl)ethene, m.p. 52-54° C., | GD |
| 2-(2,3-dimethylanilino)-1,1-bis(ethoxycarbonyl)ethene, m.p. 51-52° C., | GE |
| 2-(2,4-dimethylanilino)-1,1-bis(ethoxycarbonyl)ethene, m.p. 83-84° C., | GF |
| 2-(4-dimethylaminoanilino)-1,1-bis(ethoxycarbonyl)ethene, m.p. 99-101° C., | GH |
| 2-(2,4,5-trimethylanilino)-1,1-bis(ethoxycarbonyl)ethene, m.p. 82-84° C., | GI |
| 2-(2-methoxyanilino)-1,1-bis(ethoxycarbonyl)ethene, m.p. 50-52° C., | GJ |
| 2-(3-ethoxycarbonylanilino)-1,1-bis(ethoxycarbonyl)ethene m.p. 50-52° C., | GK |
| 2-(4-ethoxycarbonylanilino)-1,1-bis(ethoxycarbonyl)ethene m.p. 72-74° C., | GL |
| 2-(3-acetylanilino)-1,1-bis(ethoxycarbonyl)ethene, m.p. 85-87° C., | GM |
| 2-(4-acetylanilino)-1,1-bis(ethoxycarbonyl)ethene, m.p. 94-96° C., | GN |
| 2-(2-acetylanilino)-1,1-bis(ethoxycarbonyl)ethene, m.p. 120-122° C., | GO |
| 2-(3,4-dimethoxyanilino)-1,1-bis(ethoxycarbonyl)ethene, m.p. 54-55° C., | GP |
| 2-(2,5-dimethoxyanilino)-1,1-bis(ethoxycarbonyl)ethene, m.p. 78-80° C., | GQ |
| 2-(4-methylthioanilino)-1,1-bis(ethoxycarbonyl)ethene, m.p. 36-38° C., | GR |
| 2-(2-methylthioanilino)-1,1-bis(ethoxycarbonyl)ethene, m.p. 69-71° C., | GS |
| 2-(4-dimethylsulphamoylanilino)-1,1-bis(ethoxycarbonyl)ethene, m.p. 111-113° C., | GT |
| 2-(3-dimethylsulphamoylanilino)-1,1-bis(ethoxycarbonyl)ethene, m.p. 84-86° C., | GU |
| 2-(4-phenoxyanilino)-1,1-bis(ethoxycarbonyl)ethene, m.p. 68-70° C., | GV |
| 2-(2-phenylanilino)-1,1-bis(ethoxycarbonyl)ethene, m.p. 82-85° C., | GW |
| 2-(4-phenylanilino)-1,1-bis(ethoxycarbonyl)ethene, m.p. 92-94° C., | GX |
| 2-(3-chloro-4-fluoroanilino)-1,1-bis(ethoxycarbonyl)ethene, m.p. 57-59° C., | GY |
| 2-(4-chloro-2-bromoanilino)-1,1-bis(ethoxycarbonyl)ethene, m.p. 102-104° C., | GZ |
| 2-(4-diethylaminoanilino)-1,1-bis(ethoxycarbonyl)ethene, m.p. 71-73° C., | HA |
| 2-(2,6-diisopropylanilino)-1,1-bis(ethoxycarbonyl)ethene m.p. 79-81° C., | HB |
| 2-(2,6-dimethylanilino)-1,1-bis(methoxycarbonyl)ethene, m.p. 113-115° C., | HC |
| 2-(2-amino-5-methoxycarbonylanilino)-1,1-bis(ethoxycarbonyl)ethene, m.p. 144-149° C., | HD |
| 2-methyl-2-[2-acetamido-5-methoxyanilino]-1-ethoxycarbonylethene, | HE |
| 2-methyl-2-[4-ethoxycarbonylaminoanilino]1-ethoxycarbonylethene, | HF |
| 2-methyl-2-[4-acetamidoanilino]-1-ethoxycarbonylethene, | HG |
| 2-methyl-2-[4-methoxyanilino]-1-ethoxycarbonylethene, | HH |
| 2-methylthio-2-(3-methoxyanilino)-1,1-bis(ethoxycarbonyl)ethene, yellow oil, | HI |
| 2-methoxy-2-(3-methoxyanilino)-1,1-bis(ethoxycarbonyl)ethene, oil, | HJ |
| 2-methoxy-2-anilino-1,1-bis(ethoxycarbonyl)ethene, m.p. 43-44° C., | HK |
| 2-methylthio-2-anilino-1,1-bis(ethoxycarbonyl)ethene, m.p. 43-44° C., | HL |
| 2-[N—(4-fluorophenyl)-N—(1,3-dioxoisoindolin-2-yl)amino]-1,1-bis(ethoxycarbonyl)ethene, m.p. 106-107.5° C., | HM |
| 2-[N—(4-fluorophenyl)-N—(1,3-dioxoisoindolin-2-ylmethyl)]-amino-1,1-bis(ethoxycarbonyl)ethene, m.p. 147-148° C., | HN |
| 2-[N—methyl-N—benzyl]amino-1,1-bis(ethoxycarbonyl)ethene, m.p. 70.5° C., | HO |
| 2-(3-methoxyanilino)-1,1-bis(ethoxycarbonyl)ethene, | HP |
| 2-[N—phenyl-N—1,3-dioxoisoindolin-2-yl)amino]-1,1-bis(ethoxycarbonyl)ethene, | HQ |
| 2-[N—(3-methylphenyl)-N—(1,3-dioxoisoindolin-2-yl)amino]-1,1-bis(ethoxycarbonyl)ethene, | HR |
| 2-[N—(2-methylphenyl)-N—(1,3-dioxoisoindolin-2-yl)amino]-1,1-bis(ethoxycarbonyl)ethene, | HS |
| 2-[N—(2-chlorophenyl)-N—(1,3-dioxoisoindolin-2-yl)amino]-1,1-bis(ethoxycarbonyl)ethene, | HT |
| 2-[N—phenyl-N—(1,3-dioxoisoindolin-2-ylmethyl)]amino-1,1-bis(ethoxycarbonyl)ethene, and | HU |
| 2-[N—(4-methoxyphenyl)-N—(1,3-dioxoisoindolin-2-ylmethyl)]-amino-1,1-bis(ethoxycarbonyl)ethene. | HV |

The present invention includes within its scope pharmaceutical compositions which comprise at least one compound of formula I in association with a pharmaceutically acceptable carrier or coating. In clinical practice the compositions of the present invention will normally be administered orally or rectally, or parenterally, for example topically or intraarticularly.

Solid compositions for oral administration include compressed tablets, pills, dispersible powders, and granules. In such solid compositions one or more of the active compounds is mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents.

The compositions according to the invention, for oral administration, also include capsules of absorbable material such as gelatin containing one or more of the active compounds with or without the addition of diluents or excipients.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in a sterile injectable medium immediately before use. As well as the more customary intravenous and intramuscular routes, the compositions may be administered by intraarticular injection.

Compositions in the form of solutions or suspensions, if desired together with additives as described above, in water or in vegetable or other greases, paraffin or other waxes, or lacquers or creams or lotions, to be applied topically, for example to the skin area around an affected joint to relieve arthritis, are also included in the invention. They may also include additives such as nicotinamide to assist absorption.

The percentages of active ingredient in the compositions of the invention may be varied, it being necessary that they should constitute a proportion such that a suitable dosage for the desired effect shall be obtained. Obviously several unit dosage forms may be administered at about the same time. Generally the compositions should contain 0.1% to 80% by weight of active ingredient, especially when in tablet form.

The dose employed depends upon the desired effect, the route of administration and the duration of the treatment. In the adult, the doses are generally between 0.01 and 100 mg (preferably orally between 0.1 and 10 mg, or intramuscularly, intravenously or intraarticularly between 0.01 and 10 mg) of the compounds of formula I per kg body weight per day.

The compounds of formula I may be administered each day or, according to the wishes of the medical practitioner, less often, e.g. weekly.

The present invention provides a method of treating disorders, e.g. arthritic disorders, in man which comprises administering to the patient an amount of a compound of formula I sufficient to combat the disorder.

The following Composition Example illustrates pharmaceutical compositions according to the present invention.

COMPOSITION EXAMPLE 1

Capsules for oral administration were made up in the usual manner by filling No. 2 size gelatin capsules each with 155 mg of the following composition:

1,1-bis(4-chlorophenylsulphonyl)-2-(pyrid-2-ylmethylamino)ethene: 50 mg potato starch: 100 mg magnesium stearate: 2.5 mg Aerosil: 2.5 mg Similar compositions can be prepared by the use of any of the other compounds of formula I.

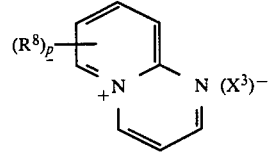

FIG. VIII

We claim:

1. The compound: 1,1-bis(phenylsulfonyl)-2-(thiazol-2-ylamino)-ethene.

2. A pharmaceutical composition which comprises, as active ingredient, a compound according to claim 1, or a pharmaceutically acceptable salt thereof, in association with a pharmaceutical carrier or coating.

3. A method for the treatment of an arthritic disorder which comprises administering to a patient an effective amount of a compound according to claim 1 or a pharmaceutically acceptable salt thereof.

* * * * *